United States Patent [19]

Muller et al.

[11] 4,256,541
[45] Mar. 17, 1981

[54] PRODUCTION OF ANYDROUS ALCOHOL

[75] Inventors: Werner C. Muller, Dobbs Ferry, N.Y.; Franklyn D. Miller, Cincinnati, Ohio

[73] Assignee: National Distillers and Chemical Corp., New York, N.Y.

[21] Appl. No.: 43,189

[22] Filed: May 29, 1979

[51] Int. Cl.³ .................. C07C 29/26; C07C 31/08
[52] U.S. Cl. ..................... 203/19; 203/25; 203/27; 203/71; 203/DIG. 13
[58] Field of Search ............. 260/449.5; 203/21, 22, 203/19, 25, 27, 71, 73, 74, 75, 77, 78, 80, 81, 82, 84, DIG. 13, DIG. 23, DIG. 19

[56] References Cited

U.S. PATENT DOCUMENTS

| | | | |
|---|---|---|---|
| 1,860,554 | 5/1932 | Ricard et al. | 203/27 |
| 3,239,435 | 3/1966 | Conseiller et al. | 203/DIG. 23 |
| 3,442,770 | 5/1969 | Wentworth et al. | 203/25 |
| 3,445,345 | 5/1969 | Katzen et al. | 203/25 |

*Primary Examiner*—Frank Sever
*Attorney, Agent, or Firm*—Kenneth D. Tremain

[57] ABSTRACT

Substantially anhydrous (absolute) ethanol is economically distilled at high thermal efficiency from any dilute feedstock such as, for example, a fermentate ("beer") or the ethanol obtained from the hydration of ethylene in apparatus including a rectifying column for concentrating the ethanol, an anhydrous column for azeotropically distilling the ethanol and a decanter for separating the azeotrope-forming agent from the aqueous ethanol. Thermal values which would otherwise be lost in overhead vapors and/or stillage effluent are utilized for preheating the ethanol feed thereby leading to a significant improvement in overall thermal efficiency. Low boiling impurities, e.g., ethyl acetate, which may be present in the feed and which could interfere with proper operation of the decanter are removed from the feed to the extent necessary in a heads stripping column operated with heat supplied from the rectifying column. During the concentration procedure, the higher boiling impurities which may be present in the feed, e.g., fusel oil, are removed from the rectifying column as a liquid sidestream. Additional features providing still greater process efficiency include the operation of the anhydrous column under elevated pressure to permit the recovery of heat for running the rectifying column and the use of cyclohexane as the azeotrope-forming agent.

8 Claims, 1 Drawing Figure

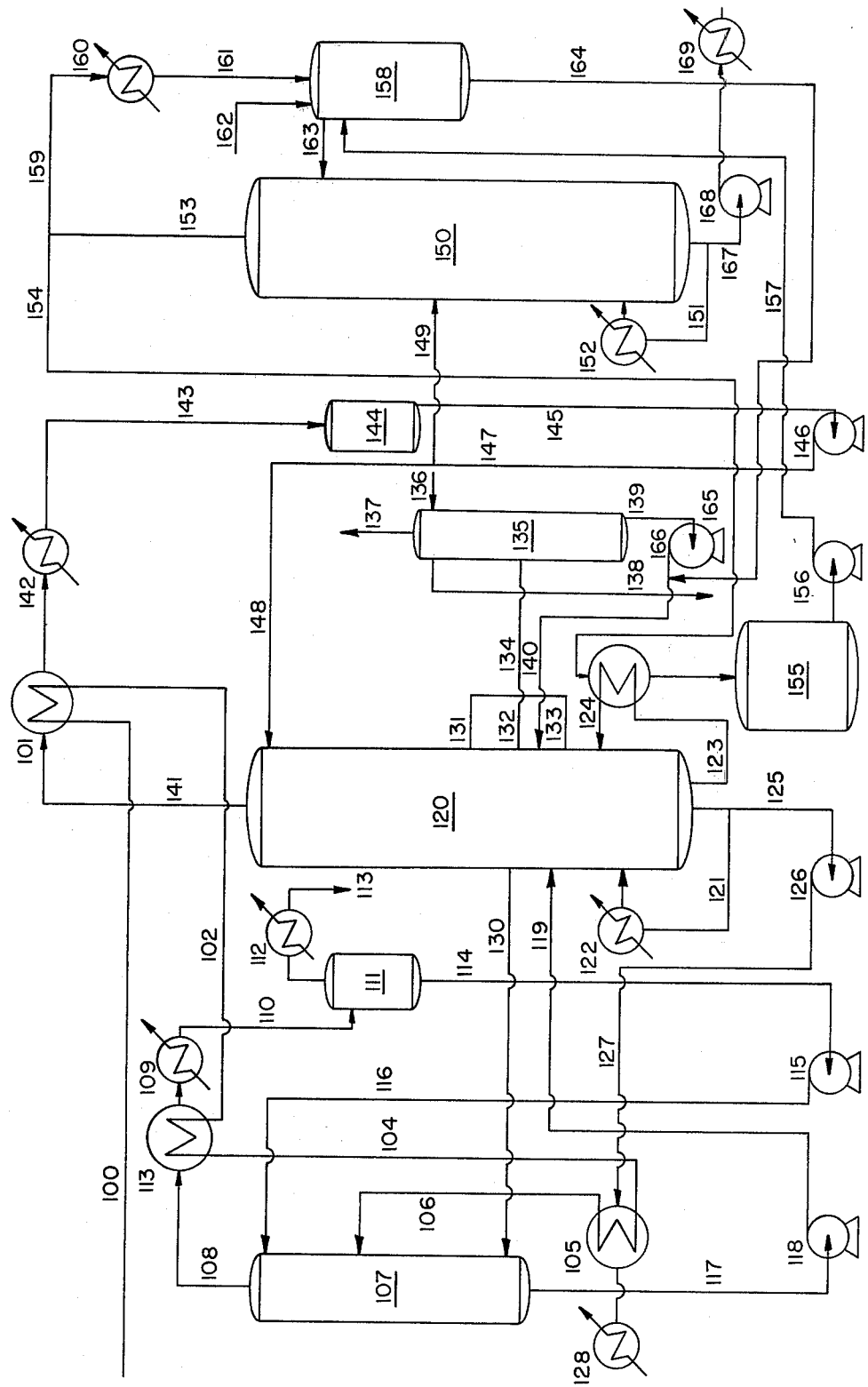

PRODUCTION OF ANYDROUS ALCOHOL

BACKGROUND OF THE INVENTION

1. Field of the Invention

This invention relates to the field of processes of distillation and, more particularly, to processes for the recovery by distillation of anhydrous ethanol from a dilute aqueous feedstock.

2. Description of the Prior Art

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity and versatility.

The various operations in processes for obtaining ethanol from such recurring sources as cellulose, cane sugar, amylaceous grains and tubers, e.g., the separation of starch granules from non-carbohydrate plant matter, the chemical and/or enzymatic hydrolysis of starch to fermentable sugar (liquefaction and saccharification), the fermentation of sugar to provide a dilute solution of ethanol ("beer") and the recovery of anhydrous or concentrated ethanol by distillation, have been modified in numerous ways to achieve improvements in product yield, production rates and so forth. For ethanol to realize its vast potential as a partial or total substitute for petroleum fuels or as a substitute chemical feedstock, it is necessary that the manufacturing process be as efficient in the use of energy as possible so as to maximize the energy return for the amount of ethanol produced and enhance the standing of the ethanol as an economically viable replacement for petroleum based raw materials.

To date, however, relatively little concern has been given to the energy requirements for manufacturing ethanol, especially with regard to the ultimate distillation operation which is the most energy intensive procedure in the ethanol production sequence whether the ethanol be derived from a petroleum or vegetative source.

The substitution of alcohol for at least a portion of petroleum based fuels is particularly critical for developing economies where proven domestic petroleum reserves are limited, such as in India and Brazil and these nations have therefore increasingly emphasized the production of alcohol from vegetative sources. The most common subject operation employs cane sugar in a fermentation-distillation operation which conveniently utilizes the bagasse by-product as a fuel source. Cassava or manioc (*Manihot utilissima Pohl*) as a source of starch has also been considered for conversion into alcohol (see "Brazil National's Alcohol Programme" Jackson, ed. Process Biochemistry, June 1976, pages 29–30).

Processes for the azeotropic distillation of a dilute ethanol feed to provide absolute alcohol are well known (viz., U.S. Pat. Nos. 1,583,314; 1,486,717; 1,586,732; 1,670,053; 1,761,779; 1,763,722; 1,830,469; 1,873,005; 1,935,529; 2,050,513; 2,386,058; 2,640,017; 2,695,867; 3,404,186; and 3,960,672). In a typical anhydrous distillation process, an aqueous alcohol stream is combined with benzene (or other azeotrope-forming liquid), and the mixture is heated in a distillation column to provide a ternary vapor mixture containing ethanol, benzene and water at the top of the column, a binary mixture of alcohol and benzene in the middle of the column and absolute ethanol at the bottom of the column. Part of the vapors at the head of the column are condensed and the condensate is returned to the top of the distillation column as reflux. The remaining part of the vapors are condensed and separated into a benzene-rich upper layer which is returned to the distillation column and an aqueous alcohol-rich lower layer from which residual benzene is removed and recycled. No attempt is made in this and similar anhydrous distillation processes to maximize the recovery of thermal values in an effort to minimize the overall consumption of energy.

SUMMARY OF THE INVENTION

In accordance with the process herein for obtaining substantially anhydrous ethanol from a dilute aqueous ethanol feed employing a heads stripping column as may be necessary for the removal of low boiling impurities which would otherwise interfere with phase separation in a decanter, a rectifying column for the concentration of the ethanol and having provision as may be necessary for the removal of high boiling impurities which would otherwise accumulate in said column, an anhydrous column for the removal of substantially all of the water remaining in the concentrated ethanol by azeotropic distillation, and a decanter in which there is formed an upper phase or layer containing the bulk of an azeotrope-forming agent together with minor amounts of ethanol and water and a lower phase or layer largely made up of water, a small amount of ethanol and azeotrope-forming agent, a dilute aqueous ethanol feed is preheated prior to introduction into the rectifying column by thermal values recovered from the overhead vapor and/or bottoms ("stillage") therefrom. The ethanol, concentrated to about 180° proof or higher in the rectifying column, is then azeotropically distilled in the anhydrous column operated under substantially elevated pressure so that thermal values recovered therefrom can be used for the operation of the rectifying column, to provide substantially anhydrous ethanol bottoms with separation of the azeotrope-rich phase from the water-rich phase in the condensed overhead vapors of the anhydrous column being carried out in the decanter.

Should the ethanol feed contain low boiling impurities which would act as mutual solvents for the azeotrope-rich phase and the ethanol-rich phase in the decanter making effective phase separation difficult if not impractical, the ethanol feed is first subjected in an extractive distillation step in the heads stripping column which is operated with thermal values recovered in a vapor sidestream taken from the rectifying column. The ethanol feed in this case can also be further preheated prior to introduction into the heads stripping column with thermal values recovered in the overhead vapors therefrom.

Another aspect of the present invention resides in the use of cyclohexane as the azeotrope-forming agent whether or not the anyhdrous column is operated at or about atmospheric pressure as in prior art practice or under pressure as disclosed herein. Cyclohexane has been found to provide even clearer phase separation in the decanter compared to known and conventional azeotrope-forming agents such as benezene, toluene, and the like.

The anhydrous distillation process herein is applicable to any dilute aqueous ethanol feedstock such as "beer" obtained from fermentation (up to about 12 weight percent ethanol), ethanol obtained from the hydration of ethylene (up to 25 weight percent ethanol) or waste sulfite liquor (up to 1.5 weight percent ethanol) each of which contains low and/or high boiling impurities, or even a dilute aqueous ethanol substantially devoid of any impurities such as "return" ethanol (up to 60 weight percent ethanol). Examples of low boiling impurities frequently encountered in the feedstocks herein include ethyl acetate, biacetyl, acetaldehyde, acrolein, alcohols of from three to five carbon atoms and their esters, methanol, diethyl acetal, and so forth. Among the high boiling impurities, fusel oil and polymeric oils are especially noted. While these substances need not always be completely removed from the product anhydrous ethanol, proper management of the process herein will require so much of their removal, if present in the feedstock, as is necessary to provide trouble-free operation of the system.

BRIEF DESCRIPTION OF THE DRAWING

The accompanying drawing is a diagrammatic flow sheet of a preferred embodiment of the process of the invention.

DESCRIPTION OF THE PREFERRED EMBODIMENTS

Referring to the drawing, a dilute impure aqueous ethanol feed obtained from the fermentation of sugar, preferably sugar obtained in accordance with the process described in either of commonly assigned copending U.S. patent application Serial Nos. 043190, and 043193, both filed May 29, 1979 respectively), each filed of even date herewith, containing from about 5 to 12 weight percent ethanol and minor amounts of ethyl acetate, fusel oil and possibly other impurities, is conveyed through line 100 to and through preheater 101 which transfers thermal values recovered from the overhead vapors passing from rectifying column 120. The partially preheated feed continues through line 102 to and through preheater 103 where it picks up additional thermal values recovered from the overhead vapor passing from heads stripping column 107. Emerging from preheater 103, the feed passes through line 104 to and through preheater 105 picking up still additional quantities of heat recovered from the stillage effluent in rectifying column 120. The feed, now heated to its atmospheric boiling point of about 210° F., passes through line 106 into the top of heads stripping column 107 for removal of ethyl acetate and any other low boiling impurities which may be present. Low boiling impurities in the feed together with some ethanol and water are removed from heads stripping column 107 as overhead vapor through line 108. The vapor passes through preheater 103 giving up a portion of its heat to the ethanol feed and thereafter passes through condenser 109 resulting in the condensation of the ethanol and water vapor components of the heads stripping column overhead vapor. The aqueous ethanol enters heads stripping column reflux drum 111 through line 110, the uncondensed vapors comprising the low boiling impurities being condensed in condenser 112 and the condensate being recovered through line 113. When the anhydrous ethanol is to be used as a fuel, the low boiling impurities can be added thereto. The aqueous ethanol in reflux drum 111 passes through line 114 and is delivered by pump 115 through line 116 into the top of the heads stripping column as reflux. The aqueous ethanol effluent from the base of heads stripping column 107, now free of ethyl acetate and other light boiling impurities which might interfere with the operation of the decanter but still containing the water and fusel oil of the original feed, passes through line 117 to pump 118 and is introduced through line 119 into rectifying column 120 wherein the ethanol is concentrated to high proof and preferably to at least about 95 volume percent (190° proof). Rectifying column 120 is operated at or about atmospheric pressure and is provided with heat supplied to liquid recirculating through line 121 passing through reboiler 122 supplied with steam. When anhydrous column 150 is run at significantly elevated levels of pressure, a sufficient amount of heat is recoverable therefrom to supply most if not all of the thermal operating requirements of rectifying column 120 by heating the liquid recirculating through line 123 passing through reboiler shell 124. When anhydrous column 150 is run at or about atmospheric pressure, the total thermal operating requirements of rectifying column 120 must be satisfied with heat supplied from reboiler 122. Hot stillage passing through line 125 is conveyed by pump 126 through line 127 to preheater 105 giving up a portion of its heat to the ethanol feed. The stillage is then cooled by heat exchanger 128 and is discharged through line 129. Advantageously, the stillage which contains soluble proteins and amino acids of the original feed is recovered for use as fertilizer, animal feed or to help satisfy the nutritive requirements of yeast in an ethanol fermentation system. Sidestream vapor containing water and ethanol is conveyed from rectifying column 120 through line 130 to the base of heads stripping column 107, the thermal values in the vapor being used to operate column 107. It is preferred that only as much sidestream vapor be withdrawn from rectifying column 120 as is necessary to provide the minimum heat required to remove that amount of light boiling impurities in the ethanol feed which would interfere with proper operation of the decanter. Sidestreams containing fusel oil are taken at different levels of rectifying column 120 through lines 131, 132 and 133 and are conveyed through common line 134 to separator vessel 135 supplied with wash water through line 136. Vapor overhead in separator vessel 135 is discharged therefrom through line 137 with the fusel oil being recovered through line 138. The fusel oil can be burned as fuel or added to the product anhydrous alcohol if the nature of the use of the latter permits. The aqueous ethanol effluent passing from separator vessel 135 through line 139 is moved by pump 165 through line 166 and is combined with the aqueous phase from decanter 158 passing through line 164, the combined streams then being introduced into rectifying column 120 through line 140. The overhead vapor from rectifying column 120 passes through line 141 to and through preheater 101 giving up a portion of its heat to the ethanol feed and the vapor thereafter passes through condenser 142 with the aqueous ethanol condensate entering rectifying column reflux drum 144 through line 143. The aqueous ethanol passing from rectifying column reflux drum 144 through line 145 is driven by pump 146 through line 147 with a major portion of the stream being diverted through line 148 to the top of rectifying column 120 to serve as reflux and the product portion of the stream being conveyed through line 149 to anhydrous column 150. In the preferred embodiment which is shown, anhydrous column 150 is run at substantially superatmospheric pressure, preferably within the range of from about 60 to about 150 psig and more preferably from about 80 to about 130 psig. Heat is supplied to anhydrous column 150 by recirculating liquid in line 151 through reboiler 152 supplied with steam. Part of the ternary vapor overhead (azeotrope-forming agent, ethanol and water) passing from anhydrous column 150 through line 153 is conveyed through line 154 giving up heat in reboiler shell 124 to rectifying column liquid recirculating through line 123. The condensed liquid entering drum 155 is conveyed by pump 156 through line 157 to the top of decanter 158. Another part of the ternary vapor passing from anhydrous column 150 through line 153 is conveyed through line 159 to and through condenser 160 with the condensate entering decanter 158 through line 161. Initial azeotrope-forming agent can be supplied to the system at any convenient point such as through line 162 to decanter 158. The upper phase in decanter 158 which is rich in azeotrope-forming agent is conveyed through line 163 to the top of anhydrous column 150 to provide reflux liquid. The lower phase in decanter 158 which is rich in water passes through line 164, combines with the aqueous ethanol from separator unit 135 passing through line 166, and is conveyed to rectifying column 120 through line 140. Substantially anhydrous ethanol is recovered from the bottom of anhydrous column 150 through line 167 and is sent by pump 168 through cooler 169 to storage. While any of the azeotrope-forming agents heretofore employed for the anhydrous distillation of ethanol, e.g., benzene, toluene, etc., can be used herein with good results, it is preferred to employ cyclohexane for this purpose especially when anhydrous column 150 is operated under pressure. In the past, it has been proposed to carry out anhydrous distillation of ethanol at elevated pressure employing diethyl ether as an entraining agent. (Moeller et al., *Industrial Engineering Chemistry*, Vol. 43, No. 3, pp 711–717 (1951); Wentworth et al., *Trans. Am. Inst. Chem. Engrs.*, Vol. 39, pp 565–578 (1943) and Vol. 36, pp 785–799 (1940)). However, diethyl ether has numerous drawbacks compared to cyclohexane for this purpose. For one thing, much higher anhydrous column operating pressures would be required in order to provide sufficient heat to run a rectifying column when working with diethyl ether. For another, diethyl ether is more hazardous than cyclohexane and reasons of safety alone militate against its use. Moreover, ether gives inferior separation between ethanol and water compared to that provided by cyclohexane.

The following table sets forth the typical material balance of ethanol, water and cyclohexane in pounds per gallon of anhydrous ethanol which are present at various fluid transfer lines in the system described herein for a typical distillation operation. Anhydrous column 150 is operated at 100 psia to provide this balance.

| Description of Stream | Beer Feed | Heads Column Reflux | Heads Product | Heads Column Vapor Feed | Heads Column Bottoms | Stillage | Anhydrous Column Feed | Anhydrous Column Bottoms | Anhydrous Column Overhead | Anhydrous Column Reflux | Water Layer |
|---|---|---|---|---|---|---|---|---|---|---|---|
| Fluid Transfer Line (from the Drawing) | 100 | 116 | 113 | 130 | 117 | 127 | 149 | 168 | 153 | 163 | 164 |
| Alcohol | 6.62 | 9.15 | .13 | 2.53 | 9.15 | — | 7.24 | 6.61 | 5.53 | 4.90 | 0.63 |
| Water | 61.18 | 0.60 | .01 | 1.98 | 63.16 | 63.16 | .50 | — | 1.34 | 0.82 | 0.52 |
| Cyclohexane | — | — | — | — | — | — | .14 | .01 | 29.95 | 29.81 | 0.14 |

What is claimed is:

1. A process for obtaining anhydrous ethanol from a dilute aqueous ethanol feed containing one or more low boiling impurities in an amount which would perceptibly interfere with the proper operation of a decanter employing a heads stripping column for removal of at least as much of the low boiling impurities in the ethanol feed as is necessary to provide proper operation of the decanter, a rectifying column for concentrating the ethanol, an anhydrous column for drying the ethanol substantially to completeness using an azeotrope-forming agent, and a decanter for separating an upper phase rich in azeotrope-forming agent from a lower phase made up largely of water, which comprises:
    (a) providing means for obtaining said anhydrous ethanol consisting essentially of said heads stripping column, said rectifying column and said anhydrous column;
    (b) stripping the dilute ethanol feed in the heads stripping column operated with thermal values contained in sidestream vapor withdrawn from the rectifying column;
    (c) concentrating the stripped dilute ethanol feed in the rectifying column; and,
    (d) azeotropically distilling the concentrated ethanol in the anhydrous column operated under substantially superatmospheric pressure to provide substantially anhydrous ethanol with thermal values recovered from the anhydrous column overhead being used to satisfy part or all of the thermal operating requirements of the rectifying column.

2. The process of claim 1 wherein prior to introduction into the heads stripping column, the dilute ethanol feed is preheated with thermal values recovered from the heads stripping column overhead vapor.

3. The process of claim 1 wherein prior to introduction into the heads stripping column, the dilute ethanol feed is preheated with thermal values recovered from the rectifying column overhead vapor and/or bottoms.

4. The process of claim 1 wherein the azeotrope-forming agent is cyclohexane.

5. The process of claim 1 wherein the ethanol feed contains high boiling impurities which are removed therefrom as a liquid sidestream taken from the rectifying column.

6. The process of claim 1 wherein the ethanol feed is obtained from a fermentation process.

7. The process of claim 1 wherein the anhydrous column is operated at from about 60 to about 150 psig pressure.

8. The process of claim 7 wherein the anhydrous column is operated at from about 80 to about 130 psig pressure.

* * * * *